US008530455B2

(12) United States Patent
Spillert et al.

(10) Patent No.: US 8,530,455 B2
(45) Date of Patent: Sep. 10, 2013

(54) HEMOSTATIC EFFECTS OF GLUCONO-DELTA-LACTONE

(75) Inventors: Charles R. Spillert, West Orange, NJ (US); Debbie Persaud, Princeton, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 253 days.

(21) Appl. No.: 12/851,041

(22) Filed: Aug. 5, 2010

(65) Prior Publication Data

US 2011/0071219 A1    Mar. 24, 2011

Related U.S. Application Data

(60) Provisional application No. 61/273,589, filed on Aug. 5, 2009.

(51) Int. Cl.
*A61K 31/585* (2006.01)

(52) U.S. Cl.
USPC .......................................................... 514/175

(58) Field of Classification Search
USPC ................................................. 514/175, 822
See application file for complete search history.

(56) References Cited

U.S. PATENT DOCUMENTS

| 5,792,660 A | 8/1998 | Spillert et al. | 436/2 |
| 6,514,766 B2 | 2/2003 | Spillert et al. | 436/70 |

OTHER PUBLICATIONS

Adams et al. "Hypercoagulability in Chronic Kidney Disease is Associated with Coagulation Activation But Not Endothelial Function" Thrombosis Research 2008 123(2):374-380.
Aras et al. "The Proinflammatory and Hypercoagulable State of Diabetes Mellitus" Reviews in Cardiovascular Medicine 2005 6(2):84-97.
Asero et al. "Coagulation Cascade and Fibrinolysis in Patients with Multiple-drug Allergy Syndrome" Annals of Allergy, Asthma, and Immunology 2008 100(1):44-48.
Borensztajn et al. "Protease-activated Receptors, Apoptosis and Tumor Growth" Pathophysiology of Haemostasis and Thrombosis Aug. 2007 36(3-4):137-147.
Bouwman et al. "Procoagulant and Inflammatory Response of Virus-infected Monocyte" European Journal of Clinical Investigation 2002 32:759-766.
Boyles, S. "Diabetes Complications Cost Billions" WebMD Apr. 4, 2007.
Chang et al. "Hemorheological Mechanisms in Alzheimer's Disease" Microcirculation 2007 14:627-634.
Ehses et al. "Increased Number of Islet Associated Macrophages in Type 2 Diabetes" Diabetes 2007 56:2356-2370.
Forrester, J. S. "Common Ancestors: Chronic Progressive Diseases Have the Same Pathogenesis" Clinical Cardiology 2004 27(4):186-190.
Han et al. "Proteomic Analysis of Active Multiple Sclerosis Reveals Therapeutic Targets" Nature 2008 451:1076-1081.
Heron, M. "Deaths: Leading Causes for 2004" National Vital Statistics Reports 2007 56:1-95.
Khorana et al. "Tissue Factor, Angiogenesis and Thrombosis in Pancreatic Cancer" Journal of Clinical Oncology 2006 24(3):484-490.
Krupinski et al. "Blood-borne Tissue Factor Activity Predicts Major Cerebrovascular Events in Patients Undergoing Carotid Endarterectomy: Results from a 1-year Follow-up Study" Cerebrovascular Disease 2008 25(1-2):32-39.
Mantovani et al. "Cancer Related Inflammation" Nature 2008 454:436-444.
McCullough et al. "Direct Correlation Between Injury Severity and Two Markers of Functional Status of the Immune System" Circulatory Shock 1990 31:309-316.
Milsom et al. "Tissue Factor and Cancer" Pathophysiology of Haemostasis and Thrombosis Aug. 2007 36(3-4):160-176.
Mozaffarian et al. "Incidence of New Onset Diabetes and Impaired Fasting Glucose in Patients with Recent Myocardial Infarction and the Effects of Clinical Lifestyle Risk Factors" Lancet 2007 370:667-675.
Olsson et al. "The Pancreatic Islet Endothelial Cell: Emerging Roles in Islet Function and Disease" The International Journal of Biochemistry and Cell Biology 2006 38(4):492-497.
Patsouris et al. "Ablation of CD11c-positive Cells Normalizes Insulin Sensitivity in Obese Insulin Resistant Animals" Cell Metabolism 2008 8(4):301-309.
Prandoni et al. "Prophylaxis of Catheter-related Thrombosis in Cancer Patients" Lancet 2009 3273:523-524.
Prodanovich et al. "Association of Psoriasis with Coronary Artery, Cerebrovascular and Peripheral Vascular Diseases and Mortality" Archives of Dermatology 2009 145(6):700-703.
Sousou et al. "New Insights into Cancer-association Thrombosis" Arteriosclerosis, Thrombosis and Vascular Biology 2009 29:316-320.
Spillert et al. "Increased Thromboplastin Production in Multiple Sclerosis: an Immunological Defect?" Annals of the New York Academy of Sciences 1986 475:345-346.
Spillert et al. "Prediction of Clinical Course in Diabetes Using a Simple Coagulation Test" Journal of the National Medical Association 1989 81(1):81-83.
Steiner, G. "Statement of the Problem" American Journal of Cardiology 2006 97(suppl):3G-8G.
Sweeten et al. "High Blood Monocyte Counts and Neopterin Levels in Children with Autistic Disorder" American Journal of Psychiatry 2003 160:1691-1693.
Triggiani et al. "Differentiation of Monocytes into Macrophages Induces the Upregulation of Histamine H1 Receptor" Journal of Allergy and Clinical Immunology 2007 119:472-481.
Visseren et al. "Procoagulant Activity of Endothelial Cells after Infection with Respiratory Viruses" Thrombosis and Haemostasis 2000 84:319-324.
Zhou et al. "Procoagulant Activity and Phosphatidylserine of Amniotic Fluid Cells" Thrombosis and Haemostasis 2009 101:845-851.

*Primary Examiner* — Kevin E Weddington
(74) *Attorney, Agent, or Firm* — Licata & Tyrrell P.C.

(57) ABSTRACT

Glucono-delta-lactone (GDL) can be used to mediate the human blood coagulation process. In particular, GDL can be used in an assay to determine an individual's risk potential for accelerated blood clotting or as a treatment for conditions related to accelerated clotting potential and/or inflammatory states.

1 Claim, 2 Drawing Sheets

HEMOSTATIC EFFECTS OF GLUCONO-DELTA-LACTONE

This application claims benefit of priority to U.S. Provisional Application Ser. No. 61/273,589, filed Aug. 5, 2009, the content of which is incorporated herein by reference in its entirety.

This invention relates to the use of glucono-delta-lactone (GDL) to mediate the human blood coagulation process. In particular, GDL can be used in an assay to determine an individual's risk potential for accelerated blood clotting or as a treatment for conditions related to accelerated clotting potential and/or inflammatory states.

About 80% of all deaths in the US involve a disease where there is dysfunction in the blood coagulation and or immune systems, i.e. heart disorders, cancer, stroke, diabetes, etc.

It has been reported that 1% to 2% of all patients treated with anticoagulants suffer significant and possibly life-threatening bleeding. Heparin is a drug administered to patients to prevent blood clotting during surgical procedures. A standard protocol to effectively monitor the appropriate dosage administration of heparin is lacking. At present, unfractionated heparins (UFHs) and low molecular weight heparins (LMWHs) are the standard agents of care administered during numerous surgical procedures, including coronary bypass surgeries and angioplasties. However, excess heparin can induce serious side effects such as excessive bleeding, bone loss, and thrombocytopenia.

Protamine sulfate (PS) is a drug administered to patients to neutralize excess heparin after the completion of surgical procedures. PS is a complex mixture of cationic low molecular weight proteins isolated from the sperm of salmon and other fish. The positive charge of PS electrostatically neutralizes the negatively charged low molecular weight heparin (LMWH), or traditional unfractionated heparin sodium (UFH), to produce a complex salt in blood. Estimating the dose of PS for appropriate neutralization of heparins by a standard protocol is lacking. In addition, it has been reported that PS administration is largely ineffective in patients who bleed while being treated with LMWH. Excess PS produces adverse effects, which range from pulmonary hypotension, edemas, anaphylactic shock, bleeding and even death.

Therefore, a novel hemostatic agent that has anticoagulant properties and is potentially less toxic than heparin is needed.

The viscosity, or thickness, of blood has physiologic effects. If the blood gets thicker, the result is an increase in blood pressure. Certain medical conditions can change the viscosity of the blood. For instance, low red blood cell concentration, anemia, reduces viscosity, whereas increased red blood cell concentration increases viscosity. Viscosity also increases with blood sugar concentration—visualize pumping syrup. It had been thought that aspirin and related "blood thinner" drugs decreased the viscosity of blood, but studies found that they act by reducing the tendency of the blood to clot instead.

Poor blood flow has been identified as being a common link to a number of different diseases, including but not limited to scleroderma, nerve and circulation problems associated with diabetes, glaucoma, macular degeneration, Alzheimer's or vascular dementia, heat attacks and strokes, intermittent claudication, impotence, male infertility, and Raynaud's disease. Many of these diseases are treated with blood-viscosity reducing drugs such as pentoxifylline and oxypentifylline. However there remains a need for additional therapies to treat these diseases.

Figure 1:
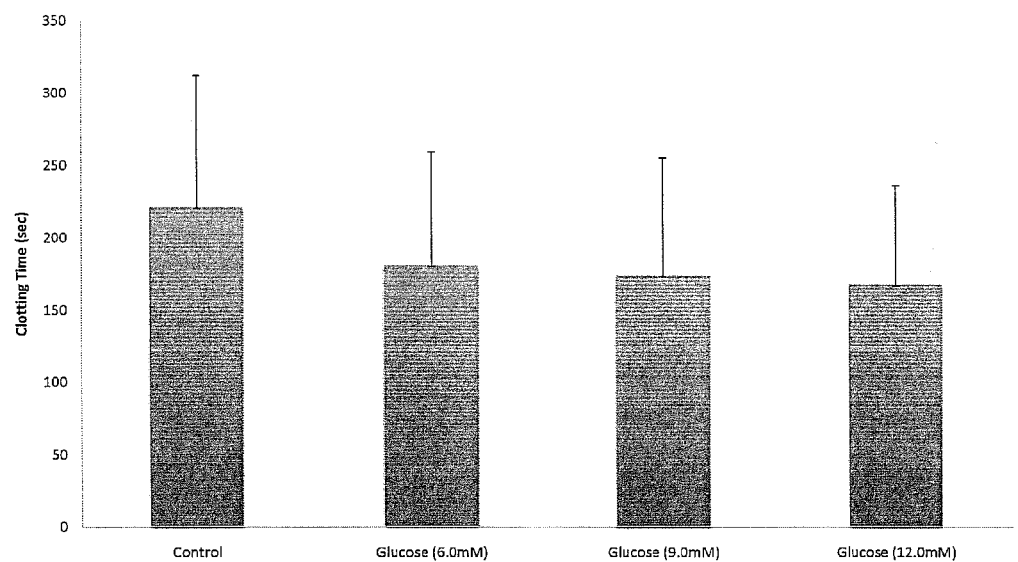
FIG. 1 is a bargraph showing excess amounts of glucose stimulate the production of tissue factor causing a reduction in whole blood clotting time.

It is an object of this invention to identify new hemostatic agents that have anticoagulant properties with less toxic side effects that heparin.

It is also an object of the invention to develop an assay that can assess an individual's risk potential for accelerated clotting, immune dysfunction and elevated blood viscosity, as well as determining the effective dose of an agent to treat such effects.

It is further an object of the invention to identify agents for the control or treatment of diseases associated with high blood viscosity.

It has now been found that glucono-delta-lactone (GDL) can act as an anticoagulant with less adverse side effects compared to the unfractionated and low molecular weight heparins.

It has also been found GDL can be used to lower blood viscosity and thus alleviate effects of diseases associated with high blood viscosity.

It has further been found that by using assays to measure clotting time, Erythrocyte Sedimentation Rate (ESR) and relative blood viscosity with and without the presence of GDL, one of ordinary skill in the art can determine a dosage of GDL effective to control such effects.

It has also been found that GDL inhibits the hypercoagulable/hyperinflammatory state induced by tissue factor.

Glucono-delta-lactone (GDL), a member of the polyhydroxyacid family, is often used as an anti-oxidant, anti-microbial, and procoagulant agent in the preparation of food and cosmetics. Thus it is an unexpected finding that GDL is an anticoagulant at certain concentrations in the blood.

GDL is an odorless white crystalline powder that is freely soluble in water (590 grams per liter of water) and hydrolyzes to form an equilibrium mixture of lactone and gluconic acid. Complete hydrolysis of GDL in water takes 40 to 60 minutes. GDL does not require refrigeration and is not susceptible to degradation at room temperatures. This stability enables GDL to be administered orally, intravenously or embedded in a transdermal delivery system.

The effects of GDL on clotting and immune systems can be monitored by relevant functional assays.

As discussed more fully below, GDL has several properties that make it easy and beneficial to use:
 1. The therapeutic dose of GDL for each individual can rapidly be determined prior to its administration.
 2. GDL reduces the procoagulant and inflammatory effect of deleterious agents generated during many disease processes.
 3. GDL shows significant anticoagulant effects when administered parenterally
 4. GDL may have beneficial properties as a topical agent (i.e. ocular, burn wound)
 5. GDL significantly reduces ESR values which may be indicative of an anti-inflammatory property The blood tests described below are capable of detecting changes in the coagulation and inflammatory status found in the patient's blood. These test procedures rapidly monitor GDL's effects (GDL converts to gluconic acid in solution) on clinically relevant pathways and therapeutic changes that may occur in a patient's status.

Clotting time of whole blood enables the contribution of both the cellular elements (leukocytes, red blood cells, platelets) and plasma (the liquid sustaining the cellular components) to be evaluated. The citrate anticoagulated sample is brought to 37° (body temperature) and calcium ion is added to initiate the coagulation cascade. Many instruments are available to determine the time between calcium addition and the formation of the blood clot (clotting time). The time for this complex phenomenon to occur can be shorter than normal (hypercoagulable), within the normal range, and longer than normal (hypocoagulable state). Some disease states are characterized by hypercoagulable clotting states and include coronary artery disease, some cancer, diabetes, multiple sclerosis, stroke etc. The hypocoagulable states include hemophilia, and patients receiving anticoagulant therapies.

When anticoagulated blood is allowed to remain undisturbed in a long thin tube, the erythrocytes (red blood cells) begin to settle. The rate these cells settle may be a biomarker of the immune system status of the donor's blood. Many chronic diseases and those which create increased morbidity and mortality show increases (larger distance of settling) in ESR than age-matched healthy individuals. The ESR can also monitor the effects of therapeutics or procedures on the patient.

The medical costs for treating a variety of chronic diseases are escalating rapidly. Part of the pathophysiological changes that occur in these states is related to up regulation of the inflammatory/coagulation systems. GDL may reduce these complications in many of the diseases that are on the leading causes of death list. The list (top ten diseases) includes heart, cancer, stroke, diabetes, Alzheimer's, influenza, kidney disease and sepsis.

Inflammation, activated macrophages and other cells appear to be responsible for the chronic progressive aspects of many diseases. Although the initiating insult varies, type II diabetes, Alzheimer's diseases and heart failure have up regulated immune cells, which result in increasing damage to many tissues and organs.

Extrinsic coagulation is initiated by tissue factor when combined with clotting factor VII (FVII) resulting from tissue injury or inflammation. This leads to a hypercoagulable state that produces thrombosis. The prevention or mitigation of TF induced-hypercoagulability may be an important cardio-protector. Anticoagulants that effectively turn off the thrombosis-inflammation circuit may prevent cardiovascular complications.

Stroke is usually a result of a thrombotic cerebral event (clot) or emboli which results in reduced blood flow and brain damage. Blood-borne tissue factor contributes to the procoagulant status of patients with a variety of vascular risk factors. The tissue factor level may be a marker for the prediction of cerebrovascular events in patients with carotid stenosis and other risk factors for stroke.

The macrophage, an up regulated monocyte, is an immune cell that has been shown to produce proinflammatory cytokines. These cytokines, in part, may alter insulin's effectiveness in individuals.

In animal studies, removal of these activated cells normalized insulin usage and decreased the inflammatory markers. The monocyte is also a reservoir for the generation of excess tissue factor, the initiator of clotting which is a major complication in the diabetic state.

The need for large amounts of blood by the pancreatic islet cells is, in part, required by it being one of the most vascularized organs with a great oxygen demand. If this necessary blood volume is not maintained (hardening of the arteries), insulin generation may become adversely affected and a diabetic state could result.

When blood monocytes leave the vasculature they are recruited to vary tissues as macrophages. The macrophages produce may biochemicals including tissue factor. The presence of this activated immune cell bearing tissue factor (the initiator of coagulant) may be indicative of the generation of a localized procoagulant state, which may enhance islet cell dysfunction and reduces effective insulin production.

Whether GDL administration may prevent the onset of this metabolic problem (diabetes) warrants study. GDL, an anticoagulant/anti-inflammatory drug candidate may inhibit damage to the beta cells by prevention of microcirculatory disturbances, thereby maintaining sufficient blood flow to these vital cells. Thrombosis, increased blood viscosity and/or the elevation of inflammatory mediators is the hallmark of the diabetic state.

Although many are of the belief that diabetes is a disease of excess sugar (glucose) in the blood, the great majority (75%) of diabetics will die of cardiovascular disease. By the year 2010, the number of diabetics worldwide will be about 220 million. This disease consumes about one-third of the entire Medicare budget and is the fastest growing disease in the United States. It is believed that earlier detection, behavioral changes and more effective treatment of diabetic complications will lower the costs and increase the population's wellness.

The yearly cost of diabetes treatment in the U.S. is about 22 billion dollars or about $10,000 per patient. Diabetics are prone to increased cardiovascular diseases and their complications (heart disease, stroke, blindness, kidney disease and amputations).

Diabetic development of coronary artery disease is the thrombotic cause of death in 75% of diabetes. This is a complex phenomena in which elevated glucose levels, elevated lipid values, high blood pressure and insulin problems lead to an accelerated rate of hardening of the arteries (atherogenesis). As the atherogenesis progresses, especially in the smaller blood vessels, the amount of critically needed blood for survival of the organs (heart, liver, kidneys etc) is reduced, which results in death of these cells and eventually the organ.

Heart Attacks (MI) significantly increase the risk for new-onset diabetes by 200 percent and impaired fasting glucose (a form of prediabetes) by 1500%. Although diabetes has long been recognized as a major contributor to death from cardiovascular disease, this report emphasizes the reverse, that is, heart attacks markedly increase the incidence of diabetic states, which in turn promotes an increased risk for this additional heart disease syndrome.

The prothrombin times (PT) of diabetics showed no significant change when compared to a control group. However, a simple whole blood recalcification time test showed that 53% of the diabetic group had clotting values (hypercoagulable state) below that of the normal range. A variety of inflammatory events are a common complication in patients with cancer. Furthermore, the inflammatory process initiated by the tumor enhances the tumor's rate of progression, decreases survival and enhances the ability for metastasis. The inflammatory/coagulation up regulation is a significant detrimental event for the patient's state of health and clinical outcome.

It is proposed that administration of GDL will have multiple beneficial effects in both the patient's quality and quantity of life.

Since GDL inhibits the procoagulant pathway induced by tissue factor, it may reduce catheter-related thrombosis in cancer patients too. This clotting complication of cancer is not effectively controlled by the current anticoagulants.

In addition, tumor cell tissue factor has been found to be elevated in pancreatic cancer and these values are correlated to increased venous thromboembolism and reduced survival time. The therapeutic targeting of tissue factor may alter both the neoplastic and thrombotic outcomes in this disease.

Tissue Factor is a key initiator of clotting and angiogenesis associated with cardiovascular disease, inflammation and neoplastic conditions. Since tissue factor plays a major role in disease progression, it may therefore be a key therapeutic target to mediate.

Cancer patients with indwelling central venous catheters are prone to a variety of thrombotic events. These complications (37% of patients) can occur in spite of use of current thromboprophylaxis regimens. GDL may mitigate this serious complication of the disease when catherization is required.

The development of Alzheimer's disease is associated with failure of a multitude of physiologic pathways. However, deterioration in the quality and quantity of brain perfused by blood (oxygen transport) must be implicated, in part, for this disabling condition.

Significant activation of the tissue factor pathway, in part, was responsible for the degree of renal dysfunction. The hypercoagulable state is associated with an inflammatory state in kidney diseases.

Activated human monocytes (virus-infected) contributes to atherosclerosis and coronary syndromes. This procoagulant activity is tissue factor-dependent and may, in part, become part of the systemic inflammatory process.

Cultured human endothelial cells when they become virus-infected change from an anticoagulant state to a procoagulant composite with the introduction of tissue factor expression.

Since GDL has been shown to have anti-tissue factor activity on human blood samples whether added (exogenous) or generated (LPS stimulation) by monocytes, the anticoagulant properties of GDL may mitigate this inflammatory/procoagulant cascade in these conditions.

We have previously found that the clotting time of patients decreased (hypercoagulable) as their trauma severity increased. Trauma initiated the inflammatory/coagulation systems with the generation of a multitude of agents from immune (cytokines) and clotting (tissue factor, thrombin) pathway cells.

In addition, the consumptive coagulation process initiated can result in organ failure and death. GDL may be a useful adjunct in the treatment of patients susceptible to sepsis.

Patients with chronic progressive multiple sclerosis have a significantly reduced clotting time when compared to apparently healthy individuals. (1) The reduced clotting time was determined on bloods incubated with saline (control) or an immunomodulator (i.e. LPS).

The immunomodulator initiated the inflammatory response of the monocyte, an immune cell, to generate tissue factor, the initiator of the blood clotting pathway and a mediator of inflammation. Sixty-seven percent of MS patients had a reduced control clotting time and 88% had an LPS-activated reduction in clotting when compared to the healthy population.

Recently, tissue factor (TF) was identified in MS lesions (plaque). This indicates a potential anticoagulant, antiinflammatory agent such as gluconic acid may enhance the activity of presently used therapies.

In autism data suggests an activation of the immune system. Is the coagulation system also activated and can GDL mitigate these effects warrants evaluation?

Amniotic fluid cells when added to blood were found to significantly reduce blood clotting times. If tissue factor is, in part at least, responsible for initiating this hypercoagulable state, then GDL may mitigate the disseminated intravascular coagulation (DIC) occurring in some patients.

Patients with multiple-drug allergy were found to have an up regulated tissue factor clotting pathway resulting in thrombin generation. Patients with chronic urticria have similar findings.

Whether GDL can mitigate the procoagulant up regulation in these disorders and other allergic conditions warrant evaluation.

Psoriasis is associated with an increasing risk of a variety of vascular diseases including atherosclerosis.

Whether the topical administration and/or systemic dosing of GDL will improve the severity of psoriasis and reduce the risk for vascular complications warrant evaluation The presence of histamine alters the function of many blood cells including monocytes. Regulation of histamine receptors (by GDL) in the monocyte/macrophage family can be important in the treatment of allergic inflammation.

GDL prolongs the clotting time of human blood exposed to tissue factor (TF) TF, the initiator of the extrinsic clotting cascade significantly reduced the clotting time from 217 to 101 seconds ($p \leq 0.001$). When GDL (3 mg/ml) was added, the clotting time was prolonged from 101 to 134 seconds ($p \leq 0.001$), thereby showing an anticoagulant property of GDL.

GDL at a concentration of 3 mg/ml was shown to significantly ($p \leq 0.05$) increase the clotting time when incubated in blood with bacterial endotoxin, when compared to control values. This reduction in a hypercoagulable/hyperinflammatory state-induced by the monocytes generation of excess tissue factor indicates that GDL has the therapeutic potential to intervene in many chronic inflammatory diseases.

Protease-activated receptors were shown to be directly correlated with cancer proliferation and malignancy. GDL was found to prolong the clotting of blood containing protease (35 µg/ml). The protease containing sample clotted in 54±44 seconds and the addition of 4 mg/ml GDL prolonged the clotting time to 154±55 seconds ($p \leq 0.01$). GDL mitigated the hypercoagulable state generated by the presence of protease.

GDL prolongs the clotting time of human blood exposed to trypsin, a pancreatic enzyme.

Trypsin is a serine protease that breaks down proteins and shortens the clotting time of blood (control 356±47 vs trypsin-treated 49±14 seconds) When GDL was added (6 mg/ml), the clotting time significantly increased to 83±19 seconds (n=4, $p \leq 0.05$), showing GDL's anticoagulant/antiinflammatory property Prolonged refrigeration of human blood produces a procoagulant condition that reduces the clotting time of the blood sample.

The mean clotting time of control blood at day 1 was 250±16 sec and the GDL (4 mg/ml) sample 432±16 seconds (n=10 $p \leq 0.001$) after four days in the refrigerator (4°) the clotting times were 177±17 and 342±32 respectively. The data show that GDL samples have a prolonged clotting time compared to control values initially and after being placed under hypothermic conditions. put at hypothermia conditions.

GDL in addition to therapeutic benefits in hypothermia may improve and prolong the quality of stored bloods or blood products to be utilized for transfusion.

The effect of GDL on in vitro human blood coagulation processes in the presence of bloods treated with UFH, LMWH, and a known activator of the coagulation cascade, Tissue Factor (TF) a known blood clotting substance present in cancerous tumors was evaluated. In addition, the effectiveness of GDL versus the standard procoagulant agent, PS, was evaluated in its ability to reduce the anticoagulant effects of bloods treated with UFH and LMWH.

The whole blood clotting times of all samples were analyzed using the Amelung KC4A Micro and Sonoclot Coagulation Analyzer. The results demonstrate that GDL acts an anticoagulant. Over the range of GDL concentrations studied (0.016 mM-66.24 mM), whole blood clotting times increased about three fold. In addition, at a concentration of 66.24 mM (11.8 mg GDL per mL blood), GDL significantly prolonged both the mean prothrombin (PT) and activated partial thromboplastin (aPTT) times compared to control blood samples ($p<0.05$). Furthermore, the data indicate that GDL enhances the anticoagulant effect of bloods treated with UFH and LMWHs (dalteparin sodium and enoxaparin sodium). GDL also reduces the procoagulant effect of TF as shown by a significant prolongation of clotting times of blood samples treated with a combination of TF and GDL compared to samples treated with TF alone ($p<0.05$).

Therefore, it is anticipated that GDL will prove to be an effective agent used to monitor or treat diseases with dysfunction in the immune response in addition to clotting disorders.

The invention also relates to a diagnostic test that monitors an individual's risk potential for accelerated clotting, immune dysfunction and elevated blood viscosity and the dose of GDL that would be an effective treatment. The coagulation-inflammation cascades are common pathophysiological pathways affected by many diseases and conditions. The test kit contains sealed vials containing appropriate concentrations of GDL. Then one ml of patient citrated whole blood (CWB) is be added, mixed, incubated and tested. One vial 1 serves as a control so that changes due to GDL can be evaluated. Possible tests performed on these aliquots include:
  Clotting time(s)
  ESR
  Relative viscosity The data enable the selection of the blood level concentration GDL that beneficially reverse the "abnormal" values found in the tests. The tests are carried out similarly to those described in U.S. Pat. Nos. 6,514,766 and 5,792,660. The appropriate modifications are apparent to one of ordinary skill in the art.

The choice of vehicle and the GDL in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the GDL may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the GDL or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the GDL in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing the GDL may be used. The GDL may be also incorporated in a gel or matrix base for application in a patch, which would allow a controlled release of compound through transdermal barrier.

Material and Methods

Human citrated whole blood (CWB) samples were gently inverted several times to ensure homogeneity and stored on ice to prevent protein denaturation. Ten microliters of physiologic saline was added to 490 µl of CWB (control), gently mixed, and incubated at 37° C. for 10 minutes. Coagulation was initiated by transferring 300 µl of blood sample to a cuvette containing 32 µl of 0.1 M $CaCl_2$. After gently mixing the sample and ensuring no air bubble formations in the cuvette, the whole blood clotting times were recorded on an Amelung KC4A Micro Coagulation Analyzer (Sigma Diagnostics, St. Louis, Mo., USA), a device that uses the relative displacement of a magnetic bead due to fibrin formation to determine the clotting time. In addition, the Sonoclot Coagulation Analyzer (Sienco, Wheat Ridge, Colo., USA), a mini-viscometer that is sensitive to fibrin polymer formation and fibrinolysis, was also employed to determine the whole blood clotting time. Both clinical instruments are FDA approved and used to evaluate blood coagulation processes at 37° C.

The procedure above was repeated using specified concentrations of glucono-delta-lactone (Roquette, Lestrem, France), protamine sulfate grade X (Sigma Chemical, St. Louis, Mo., USA), unfractionated heparin sodium (Sigma Chemical, St. Louis, Mo., USA), enoxaparin sodium (Lovenox®, Safoni-Aventis, Paris, France), dalteparin sodium (Fragmin®, Pharmacia & UpJohn, Kalamazoo, Mich., USA), and Tissue Factor (Sigma Chemical, St. Louis, Mo., USA). Clotting time values obtained within each study were evaluated by repeated measures analysis of variance (ANOVA) followed by Tukey-Kramer multiple comparison tests. All statistical analyses were assessed using two-sided paired Student t tests and significance was defined as p<0.05.

Results and Discussion

I. GDL Dose Response Curve

The mean clotting times of citrated whole blood samples containing saline, 2.90 µg GDL/mL, 23.00 µg GDL/mL, 184.00 µg GDL/mL, 1.48 mg GDL/mL, and 11.80 mg GDL/mL were 254.08±27.37, 246.55±28.32, 307.90±16.82, 387.33±52.36, 444.55±92.01, and 687.37±51.23, respectively.

The data suggest that increasing the concentration of GDL in blood prolongs clotting time compared to control samples. Furthermore, at concentrations greater than 184 µg GDL per mL of blood, GDL acts as a potent anticoagulant[1] (n=4, p<0.05).

No hemolysis was evident in any patient populations at the concentrations of GDL employed in the described experiments. In addition, a GDL Dose Response Curve was evaluated in plasma and a similar anticoagulant effect was observed. Although, the clotting times of control plasma samples along with plasma samples treated with GDL had a longer clotting time compared to corresponding whole blood samples.

II. Comparison of GDL Versus PS on Reducing the Anticoagulant Effect of Bloods Treated with UFH and LMWH In order to investigate GDL's capacity to neutralize the anticoagulant effect of heparinized blood, mean clotting times of GDL along with the standard procoagulant agent of care, protamine sulfate (PS), were evaluated on bloods treated with unfractionated heparin sodium (UFH) and a low molecular weight heparin (LMWH), dalteparin sodium. Mean clotting times shown in Table 1, suggest that both PS and GDL significantly reduce the anticoagulant effect of bloods treated with UFH (p<0.05). However, the data indicates that PS has a more significant effect on reducing the clotting

TABLE 1

Mean ± S.D. clotting times of heparinized bloods treated with GDL and PS (n = 8).

| Reagent(s) per mL CWB | Mean Clotting Times (s) |
|---|---|
| Control | 264.38 ± 24.17 |
| 2 µg GDL | 271.13 ± 24.83 |
| 2 µg PS | 294.26 ± 22.92 |
| 0.2 Unit UFH | 648.54 ± 55.31 |
| 0.2 Unit UFH: 2 µg GDL | 572.51 ± 45.94 |
| 0.2 Unit UFH: 2 µg PS | 464.71 ± 42.83 |
| 0.2 Unit LMWH | 512.46 ± 47.46 |
| 0.2 Unit LMWH: 2 µg GDL | 456.15 ± 47.45 |
| 0.2 Unit LMWH: 2 µg PS | 433.96 ± 56.96 | time of blood treated with UFH compared to GDL (p<0.05) shown in Table 1. Furthermore, the data suggests that PS significantly reduces the anticoagulant effect of bloods treated with dalteparin sodium (p<0.05). In contrast, GDL was not shown to markedly neutralize the anticoagulant effect of bloods treated with LMWH (p>0.05).

III. GDL Dose Response Curve on Bloods Spiked with 0.3 Unit UFH

In order to investigate whether increasing the concentration of GDL (greater than 2 µg per mL heparinized blood) would have a more profound procoagulant effect on neutralizing the anticoagulant effect of bloods treated with unfractionated heparin sodium (UFH), the mean clotting times of increasing concentrations of GDL were evaluated on bloods treated with 0.3 Unit UFH.

TABLE 2

Mean ± S.D. clotting times of 0.3 Unit unfractionated heparinized (UFH) bloods treated with increasing concentrations of GDL (n = 5).

| Reagent(s) per mL CWB | Mean Clotting Times (s) |
|---|---|
| Control | 246.56 ± 36.06 |
| 0.3 Unit UFH | 507.52 ± 85.26 |
| 0.3 Unit UFH: 2.9 µg GDL | 415.10 ± 101.63 |
| 0.3 Unit UFH: 10 µg GDL | 498.94 ± 81.24 |
| 0.3 Unit UFH: 23 µg GDL | 675.34 ± 129.28 |
| 0.3 Unit UFH: 184 µg GDL | 825.96 ± 160.74 |
| 0.3 Unit UFH: 1.48 mg GDL | 926.44 ± 192.03 |
| 0.3 Unit UFH: 11.8 mg GDL | 1197.89 ± 114.32 |

Mean clotting times shown in Table 2 suggest that increasing the concentration of GDL surprisingly prolongs the anticoagulant effect of unfractionated heparin. This phenomenon was not seen in previous experiments, where at concentrations of less than 3 µg GDL per mL unfractionated heparinized blood, GDL showed a significant procoagulant effect on reducing the clotting time of blood treated with 0.2 Unit UFH/mL. The data indicate at concentrations equal to and greater than 184 µg GDL per mL of blood, GDL significantly prolongs the clotting time of UFH compared to UFH administered alone (p<0.05). Therefore, at concentrations greater than 184 µg GDL per mL of blood, GDL is not only a potent anticoagulant on its own but potentiates the anticoagulant effect of UFH.

IV. GDL Dose Response Curve on Bloods Spiked with 0.3 Unit LMWH

Since prior data indicated that GDL potentiates the anticoagulant effect of UFH at higher doses, the investigation of whether increasing the concentration of GDL would also prolong the clotting time of low molecular weight heparin was pursued. The mean clotting times of increasing concentrations of GDL were evaluated on bloods treated with 0.3 Unit LMWH (enoxaparin sodium). Mean clotting times shown in Table 3 suggest at low doses (concentrations less than 10 µg GDL per mL low molecular weight heparinized blood), GDL shows a trend of reducing the clotting time of bloods treated with 0.3 Unit enoxaparin sodium (p>0.05). This data correlates with prior experiments, demonstrating GDL's inability at low doses to markedly neutralize the anticoagulant effect of bloods treated with another LMWH, dalteparin sodium. On the other hand, higher doses of GDL (concentrations greater than 1.48 mg GDL per low molecular weight heparinized blood) significantly prolongs the anticoagulant effect of bloods treated with enoxaparin sodium compared to bloods treated with enoxaparin sodium alone (p<0.05).

TABLE 3

Mean ± S.D. clotting times of enoxaparin sodium heparinized (LMWH) bloods treated with increasing concentrations of GDL (n = 4).

| Reagent(s) per mL CWB | Mean Clotting Times (s) |
|---|---|
| Control | 201.00 ± 32.41 |
| 0.3 Unit LMWH | 307.67 ± 45.44 |
| 0.3 Unit LMWH: 2.9 µg GDL | 240.73 ± 29.58 |
| 0.3 Unit LMWH: 10 µg GDL | 294.50 ± 46.16 |
| 0.3 Unit LMWH: 23 µg GDL | 336.28 ± 51.79 |
| 0.3 Unit LMWH: 184 µg GDL | 381.23 ± 61.83 |
| 0.3 Unit LMWH: 1.48 mg GDL | 442.45 ± 63.38 |
| 0.3 Unit LMWH: 11.8 mg GDL | 542.88 ± 54.17 |

V. Effect of GDL on Increasing the Anticoagulant Effect of Bloods Treated with UFH and LMWH Prior experiments have demonstrated the capacity of GDL to prolong the clotting time of blood used as a single agent. In addition, the data indicate that GDL potentiates the anticoagulant effect of blood treated with unfractionated and low molecular weight heparin. In the previous experiments, the whole blood clotting times were measured using the Amelung KC4A Micro, an instrument approved by the FDA to measure blood coagulation processes. Another FDA approved instrument used to measure blood coagulation and fibrinolysis is the Sonoclot Coagulation Analyzer. In order to corroborate the data demonstrating the capacity of GDL to prolong the clotting times of bloods treated with UFH and LMWH, the Sonoclot Coagulation Analyzer was used to measure the mean clotting times of a high dose of GDL on bloods treated with 0.2 Unit unfractionated heparin sodium and 0.2 Unit dalteparin sodium. Mean clotting times shown in Table 4 indicate that at the concentration of 11.8 mg GDL per mL CWB, GDL

TABLE 4

Mean ± S.D. clotting times of unfractionated heparinized (UFH) bloods and dalteparin sodium heparinized (LMWH) bloods treated with a high concentration of GDL (n = 16).

| Reagent(s) per mL CWB | Mean Clotting Times (s) |
|---|---|
| Control | 262.63 ± 49.67 |
| 11.8 mg GDL | 631.75 ± 74.55 |
| 0.2 Unit UFH | 677.25 ± 55.33 |
| 0.2 Unit UFH: 11.8 mg GDL | 852.00 ± 80.72 |
| 0.2 Unit LMWH | 549.69 ± 56.52 |
| 0.2 Unit LMWH: 11.8 mg GDL | 844.94 ± 77.99 | prolongs the clotting time of blood to the same degree as the conventional anticoagulant, 0.2 Unit UFH ($p > 0.05$). In addition, both UFH and GDL at the concentrations employed demonstrate a more profound anticoagulant effect compared to the LMWH ($p < 0.05$). Furthermore, GDL significantly prolongs the clotting times of bloods treated with unfractionated heparin and dalteparin sodium compared to bloods treated with UFH and LMWH alone ($p < 0.05$). The data correlate with whole blood clotting times that were measured using the Amelung KC4A Micro Coagulation Analyzer.

VI. Effect of GDL on Reducing the Procoagulant Effect of Bloods Treated with TF

In order to evaluate the potential of GDL's anticoagulant activity to reverse the procoagulant effect of Tissue Factor in human blood, mean clotting times of a high dose of GDL on bloods treated with 0.2% TF were evaluated (Table 5).

TABLE 5

Mean ± S.D. clotting times of bloods treated with 0.2% Tissue Factor (TF) and high concentration of GDL (n = 16).

| Reagent(s) per mL CWB | Mean Clotting Times (s) |
|---|---|
| Control | 252.25 ± 25.05 |
| 11.8 mg GDL | 618.31 ± 71.81 |
| 0.2% TF | 100.13 ± 23.10 |
| 0.2% TF: 11.8 mg GDL | 418.44 ± 80.46 |

Repeated measures of analysis of variance (ANOVA) indicated significant differences among all groups ($p < 0.05$). The combination of TF and GDL resulted in a significantly prolonged clotting time compared with TF alone ($p < 0.05$).

VII. Effect of GDL and Tissue Factor on Clotting Time

Preliminary data has indicated that (GDL) has anticoagulant properties when tested in human blood. This study evaluated whether GDL has anticoagulant properties in the presence of Tissue Factor (TF), a major initiator of abnormal blood clotting in many diseases. This coagulation study was performed on human citrated whole blood (CWB) and the clotting times were determined instrumentally. The CWB aliquots with TF had the shortest clotting time followed by the CWB plus the combination of the TF and the GDL, subsequently followed by the control CWB and finally the CWB with the GDL. The TF shortened the clotting time while the GDL prolonged it. The combination GDL and TF increased the clotting time above that of TF alone, indicating that GDL had an anticoagulant effect in the presence of TF ($p < 0.01$). The results are set forth in Table 6.

| Mean Clotting Time (sec) n = 9 | | |
|---|---|---|
| Samples | Mean | S.D. |
| A CWB | 217 | 55 |
| B CWB + TF | 101 | 20 |
| C CWB + GDL | 270 | 62 |
| D CWB + TF + GDL | 134 | 22 |

VIII. Effect of GDL on PT and aPTT

In order to evaluate what contact coagulation pathways are inhibited and thereby contributing to the anticoagulant effect of GDL, the mean prothrombin (PT) and activated partial thromboplastin (aPTT) times of increasing concentrations of GDL were evaluated by the UMDNJ University Hospital Hematology Lab (Table 7).

TABLE 7

Mean ± S.D. prothrombin (PT) and activated partial thromboplastin (aPTT) times of bloods treated with a low and high dose of GDL (n = 3).

| Reagent(s) per mL CWB | (PT, aPTT) |
|---|---|
| Control | (15.10 ± 3.47, 29.63 ± 8.24) |
| 50 µg GDL | (13.37 ± 0.12, 32.93 ± 3.15) |
| 11.8 mg GDL | (83.00 ± 29.45, 104.13 ± 34.29) |

The data indicates that at the smaller concentration, 50 µg GDL per mL of blood, GDL does not affect the PT or the aPTT values compared to control blood samples ($p > 0.05$). On the other hand, a higher concentration of GDL (11.8 mg GDL per mL blood) significantly prolongs both the PT and aPTT values compared to untreated and low dose GDL blood samples ($p < 0.05$). This data correlates with the profound prolongation of clotting time, demonstrated with the addition of 11.8 mg GDL per mL CWB seen in prior experiments.

IX. Effect of GDL on Erythrocyte Sedimentation Rate (ESR)

The ESR is the distance red blood cells settle in anticoagulated blood in one hour (mm/hr). These test results are elevated in many diseases that affect the immune system (infections, arthritis, cancer, heart diseases).

GDL (n=13 samples of blood) at concentrations of about 3 mg/ml or greater significantly reduces the ESR value in vitro. The ESR values for (control) 0.0 mg/ml GDL is 20±13; 0.1 mg/ml GDL is 18±14; 3.0 mg/ml GDL is 16±12 and 6.0 mg/ml is 15±12. The p value for ESR values of 3.0 and 6.0 mg/ml were significantly ($p < 0.01$) reduced compared to control values.

GDL mitigates the increased sedimentation rate induced in human bloods incubated with methylcelluose (MC)

Effect of GDL on Methylcellulose (MC)-Accelerated ESR

| Control (MC 0.1%) | 40.5 mm |
|---|---|
| GDL (1 mg/ml) | 34.6 mm |

(N = 8, p < 0.05)

Effect of GDL on ESR

| A) Water (control) | 19.8 mm |
|---|---|
| B) MC (0.1 mg/ml) | 39.6 |
| C) GDL (1 mg/ml) | 9.6 |
| D) MC + GDL | 30.1 |

Thus, MC increases ESR compared to water (B vs. A). GDL reduces ESR compared to control (C vs. A). GDL reduces ESR compared to MC (B vs. D)

The Effect of Histamine Concentration on Human Blood Clotting Time

Histamine Study I

Human citrated whole bloods (n=9) were mixed with histamine at the following final concentrations in blood: A) 0 µg/ml (control, B) 20 µg/ml C 40 µg/ml and D) 60 µg/ml. The instrumentally determined clotting times after 10 minutes of incubation at 37° were A) 300±72; B) 252±61; C) 230±49 and D) 205±71 seconds. All histamine containing samples clotted at a significantly reduced time than the control value ($p \leq 0.05$). These results indicate that histamine, an inflammatory mediator, produces a procoagulant effect in whole blood. This hypercoagulability may potentiate histamine's inflammatory capability by releasing additional deleterious agents.

Histamine Study II

The effect of nanogram concentrations of histamine on blood clotting (n=8) was determined. The clotting times for A) 0 ng/ml (control), B) 20 ng/ml, C) 40 ng/ml and D) 60 ng/ml were performed. The clotting times are as follows: A) 264±80, B) 257±105, C) 240±42 and D) 235±73 seconds respectively. Samples B and C were not significantly different than control values (p=NS) However, the D sample (60 ng/ml histamine) was significantly reduced ($p \leq 0.01$) when compared to control (A) value for clotting time.

Histamine Study III

To determine whether the anticoagulant/anti-inflammatory properties of GDL can mitigate the procoagulant effect of histamine on blood clotting time (n=8).
The test samples contained:
A) 0 ng/ml histamine, 0 mg/ml of GDL (control)
B) 60 ng/ml histamine, 0 mg/ml GDL
C) 60 ng/ml histamine, 3 mg/ml GDL
D) 60 ng/ml histamine, 4 mg/ml GDL The clotting times were:
A) 264±38, ) 220±39, C) 305±30, and D) 325±53 seconds respectively.
B) (histamine) significantly reduced the clotting time compared to A (control).
Samples C and D containing GDL in addition to histamine significantly prolonged the clotting time when compared to histamine alone (B) ($p \leq 0.01$) GDL shows anticoagulant/anti-inflammatory properties in mitigating the procoagulant effects shown by histamine, an inflammatory agent in addition to being a procoagulant.

Histamine Study IV

To determine whether GDL shows anticoagulant properties against blood samples in which histamine was the first agent added to the blood sample
The test samples (n=8) contained:
A) 0 µg/ml histamine, 0 mg/ml GDL
B) 1 µg/ml histamine, 0 mg/ml GDL
C) 1 µg/ml histamine, 1 mg/ml GDL
D) 1 µg/ml histamine, 2 mg/ml GDL
The clotting times were:
A) 306±108, B) 253±136, C) 297±113, D) 304±121 seconds respectively. The 1-tail p values are as follows: B was significantly reduced compared to A ($p \leq 0.05$). C and D were significantly prolonged ($p \leq 0.05$) when compared to B.
The results show:
1. that GDL mitigates the procoagulant effects of histamine (even when added to blood after the latter).
2. GDL is an effective anticoagulant/anti-inflammatory agent at low concentrations.

Diabetes Studies

Figure 2:
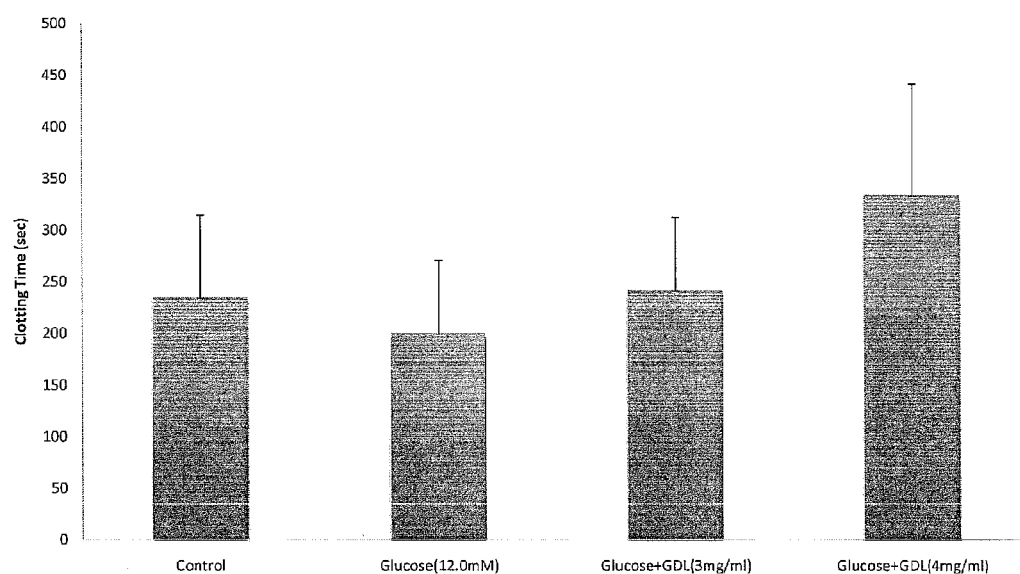
FIG. 2 is a bargraph showing glucono-delta-lactone acts as an anticoagulant, prolonging clotting time even in the presence of excess glucose.

Experimental Design
Citrated whole blood samples were obtained from the University Hospital's clinical laboratory with prior IRB approval. Samples were treated with different concentrations of glucose (6.0 mM, 9.0 mM, and 12.0 mM) to determine if a dose-response relationship existed between the glucose concentration and clotting time. Clotting times were then recorded using a Diagnostica Stago ST4 Coagulation Analyzer.
After the dose-response was established, more blood samples were obtained and treated with two doses of GDL (3 mg/ml and 4 mg/ml). The samples were incubated for 10 minutes prior to the addition of glucose (12.0 mM). After 24 hours, clotting times were recorded using a Diagnostica Stago ST4 and Sonoclot Coagulation Analyzer (FIG. 2).
Results and Discussion

Effect of GDL on Glucose-Accelerated Clotting Time

| Control | 236 ± 79 seconds |
|---|---|
| Glucose | 201 ± 71 |
| Glucose ± GDL (3 mg/ml) | 243 ± 70 |
| Glucose ± GDL (4 mg/ml) | 334 ± 107 |

Thus GDL significantly reverses the hypercoagulable state induced in human blood incubated with exogenous with glucose.

Tissue factor is the primary initiator of blood coagulation. Excess amounts of glucose stimulate the production of tissue factor causing a reduction in whole blood clotting time (FIG. 1).

Glucono-delta-lactone acts as an anticoagulant, prolonging clotting time even in the presence of excess glucose (FIG. 2).

The clotting time of whole blood decreases as blood glucose levels rise.

Glucono-delta-lactone is a safe and effective anticoagulant, capable of preventing coagulation caused by excess glucose levels in the blood.

Animal Studies

GDL has shown significant anticoagulant properties on human blood in Vitro. In addition, extensive safety studies of GDL have been carried out in humans. GDL has been issued GRAS status (Generally Recognized As Safe) by the FDA for use in foods and other products. However, none of the reported studies evaluate GDL for the potential pharmaceutical properties we have disclosed. Therefore, animal testing for efficacy as an anticoagulant in mice will serve as an initial "proof of concept" for GDL.

Experimental

GDL dissolved in saline or a control (saline) was injected intraperitoneally into pentobarbital anesthetized mice. Thirty minutes later, a sample of cardiac blood was collected with minimal trauma and the clotting time determined instrumentally. The concentration of GDL employed was 500 mg/kg body weight. A significant increase in clotting time (unpaired t-test) in GDL recipients was found when compared to the control group. This data confirms GDL's efficacy as an anticoagulant agent in vivo.

Clotting Time (Seconds)

| Control (n = 4) | GDL recipients (n = 8) |
|---|---|
| 124 ± 21 | 221 ± 62 |

$p \leq 0.01$

GDL significantly prolongs the clotting time in mice when administered parenterally.

When the GDL is administered orally there was no significant effect on clotting time.

Clotting Time (Seconds)

| Control (n = 4) | GDL recipients (n = 8) |
|---|---|
| 196 ± 25 | 199 ± 333 | p = NS

This anticoagulant property of GDL may become a therapeutic agent alone or in combination with other drugs when administered intraperitoneally, depending upon clinical findings.

Modifications and variations of the present invention will be obvious to those of skill in the art from the foregoing detailed description. Such modifications and variations are intended to come within the scope of the following claims.

REFERENCES

Heron M. Deaths: leading causes for 2004 National Vital Statistics reports. 2007 56:1-95

Forester J S. Common Ancestors: Chronic progressive diseases have the same pathogenesis. Clin Card (2204 27, 186-190

Krupinski J et al. Blood-borne tissue factor activity predicts major cerebrovascular events in patients undergoing carotid endarterectomy: results from a 1-year follow-up study. Cerebrovascular disease. 2008; 25(1-2):32-9.

Macrophages: New target for diabetes therapy. Olefsky J M et al. Cell Metab 2008; 8(4):301-309

Olsson R et al. The pancreatic islet endothelial cell: emerging roles in islet function and disease. Int. J. biochem cell biol. 2006; 38(4):492-497

Ehses J A et al. Increased number of islet associated macrophages in Type 2 diabetes. Diabetes 2007; 56:2356-2370.

Steiner G, et al. Medical Device Daily; Apr. 24, 2007. Statement of the problem. Am J. Cardiol 2006; 97(suppl):3G-8G Boyles S. Diabetes complications cost billions. WebMD Apr. 4, 2007

Aras R et al. The proinflammatory and hypercoagulable state of diabetes mellitus. Reviews in cardiovascular medicine. 2005; 6(2):84-87.

Mozaffarian D et al. Incidence of new onset diabetes and impaired fasting glucose in patients with recent myocardial infarction and the effects of clinical lifestyle risk factors Lancet. 2007; 370:667-675

Spillert C R et al. Prediction of clinical course in diabetes using a simple coagulation test. J Natl Med Assoc. 1989; 81:81-83

Mantovani A et al. Cancer related inflammation. Nature 2008; 454:436-444

Khorana A A et al. Tissue factor, angiogenesis and thrombosis in pancreatic cancer. J Clin Oncol. 2006; 24(18s):4001

Milsom C et al. Tissue factor and Cancer. Pathophysiology of Haemostasis & Thrombosis 2008; 36(3-4):160-76.

Sousou T et al. New insights into cancer-associated thrombosis. Arteriosclerosis, Thrombosis and Vascular Biology. 2009; 29: 316-20.

Prandoni P et al. Prophylaxis of Catheter-related thrombosis in cancer patients. Lancet 2009:3273; 523-4

Chang C Y et al. Hemorheological mechanisms in Alzheimer's disease. Microcirculation 2007; 14: 627-34

Adams M J et al. Hypercoagulability in chronic kidney disease is associated with coagulation activation but not endothelial function. Thrombosis Research. 2008; 123 (2): 374-80

Bouwman J J et al. Procoagulant and inflammatory response of virus-infected monocyte Eur J Clin Invest. 2002; 32:759-66

Visseren F L et al. Procoagulant activity of endothelial cells after infection with respiratory viruses. Thrombosis & Haemostasis. 2000; 84:319-24

McCullough J N et al. Direct correlation between injury severity and two markers of functional status of the immune system. Circulatory Shock. 1990; 31:309-16

Spillert C R et al Increased thromboplastin production in multiple sclerosis: an immunological defect? Ann NY Acad Sci. 1986 475:345-346

Han M H et al. Proteomic analysis of active multiple sclerosis reveals therapeutic targets. Nature. 2008; 451:1076-81

Sweeten T Z et al High blood monocyte counts and neopterin levels in children with autistic disorder Amer J. Psychiatry 2003; 160:1691-3

Vine A K Recent advances in haemostasis and thrombosis Retina 29(1): 1-7, 2009

Zhou J et al, Procoagulant activity and phosphatidylserine of amniotic fluid cells. Thromb Haemost 2009; 101:485-51

Asero R et al, Coagulation cascade and fibrinolysis in patients with multiple-drug allergy syndrome Annals of Allergy, Asthma & Immunology 2008; 100 (1): 44-8

Prodanovich S, et al. Association of psoriasis with coronary artery, cerebrovascular and peripheral vascular diseases and mortality. 2009; 145: 700-03.

Triggiani M et al. Differentiation of monocyte into macrophages induces the upregulation of histamine H1 receptor. J. Allergy & Clin Immunology. 2007; 119:472-81

Ranade D et al. Effects of glucono-delta-lactone and tissue factor on clotting time. 34$^{th}$ Northeast Bioengineering Conf. 2008; 34: 213-6

Borensztajn K S et al. Protease-activated receptors, apoptosis and tumor growth Pathophysiology of Haemostasis & Thrombosis 2008 36(3-4):137-47.

The invention claimed is:

1. A method of lessening the coagulation properties of a patient's blood which comprises administering to a patient in need of anticoagulant therapy an anticoagulant effective amount of glucono-delta-lactone and lessening the coagulation properties of the patient's blood.

* * * * *